US011020412B2

(12) United States Patent
Shah et al.

(10) Patent No.: US 11,020,412 B2
(45) Date of Patent: Jun. 1, 2021

(54) PHARMACEUTICAL COMPOSITION COMPRISING DAPAGLIFLOZIN

(71) Applicant: Inventia Healthcare Limited, Mumbai (IN)

(72) Inventors: Vaibhavi Shah, Mumbai (IN); Vijayendrakumar Redasani, Thane (West) (IN); Anant Ghongade, Thane (West) (IN)

(73) Assignee: INVENTIA HEALTHCARE LIMITED, Mumbai (IN)

( * ) Notice: Subject to any disclaimer, the term of this patent is extended or adjusted under 35 U.S.C. 154(b) by 0 days.

(21) Appl. No.: 16/484,344

(22) PCT Filed: Feb. 27, 2018

(86) PCT No.: PCT/IB2018/051221
§ 371 (c)(1),
(2) Date: Aug. 7, 2019

(87) PCT Pub. No.: WO2018/167589
PCT Pub. Date: Sep. 20, 2018

(65) Prior Publication Data
US 2020/0030346 A1  Jan. 30, 2020

(30) Foreign Application Priority Data
Mar. 16, 2017  (IN) .............. 201721009146

(51) Int. Cl.
*A61K 31/70* (2006.01)
*A61K 9/20* (2006.01)

(52) U.S. Cl.
CPC ............ *A61K 31/70* (2013.01); *A61K 9/2009* (2013.01); *A61K 9/2018* (2013.01); *A61K 9/2031* (2013.01); *A61K 9/2054* (2013.01)

(58) Field of Classification Search
CPC .... A61K 31/70; A61K 9/2018; A61K 9/2031; A61K 9/2009; A61K 9/2054
USPC ......................................................... 514/23
See application file for complete search history.

(56) References Cited

U.S. PATENT DOCUMENTS

| | | |
|---|---|---|
| 6,414,126 B1 | 7/2002 | Ellsworth et al. |
| 6,515,117 B2 | 2/2003 | Ellsworth et al. |
| 6,936,590 B2 | 8/2005 | Washburn et al. |
| 7,375,213 B2 | 5/2008 | Deshpande et al. |
| 7,851,502 B2 | 12/2010 | Bindra et al. |
| 7,919,598 B2 | 4/2011 | Gougoutas et al. |
| 7,932,379 B2 | 4/2011 | Deshpande et al. |
| 8,088,743 B2 | 1/2012 | Washburn et al. |
| 8,143,289 B2 | 3/2012 | Biftu et al. |
| 8,221,786 B2 | 7/2012 | Bindra et al. |
| 8,361,972 B2 | 1/2013 | Bindra et al. |
| 8,415,297 B2 | 4/2013 | Biftu et al. |
| 8,450,286 B2 | 5/2013 | Maldonado et al. |
| 8,501,698 B2 | 8/2013 | Gougoutas et al. |
| 8,518,895 B2 | 8/2013 | Leslie et al. |
| 8,535,715 B2 | 9/2013 | Abebe et al. |
| 8,592,371 B2 | 11/2013 | Biftu et al. |
| 8,603,989 B2 | 12/2013 | Halperin |
| 8,685,934 B2 | 4/2014 | Strumph et al. |
| 8,716,251 B2 | 5/2014 | Bindra et al. |
| 8,772,328 B2 | 7/2014 | Biftu et al. |
| 8,791,077 B2 | 7/2014 | Leslie |
| 8,853,385 B2 | 10/2014 | Ueta et al. |
| 8,871,264 B2 | 10/2014 | Hallgren et al. |
| 8,951,965 B2 | 2/2015 | Biftu et al. |
| 8,952,139 B2 | 2/2015 | Henschke et al. |
| 8,999,941 B2 | 4/2015 | Henschke et al. |
| 9,006,188 B2 | 4/2015 | Marom et al. |
| 9,050,258 B2 | 6/2015 | Abebe et al. |
| 9,198,925 B2 | 12/2015 | Bindra et al. |
| 9,278,976 B2 | 3/2016 | Biftu et al. |
| 9,394,328 B2 | 7/2016 | Blatter et al. |
| 9,403,790 B2 | 8/2016 | Biftu et al. |
| 9,453,039 B2 | 9/2016 | Gougoutas et al. |
| 9,480,755 B2 | 11/2016 | Puskas et al. |
| 9,550,747 B2 | 1/2017 | Zhu et al. |
| 9,616,028 B2 | 4/2017 | Abebe et al. |
| 9,676,741 B1 | 6/2017 | Santra et al. |
| 9,834,533 B2 | 12/2017 | Hsiao et al. |
| 9,845,303 B2 | 12/2017 | Desai et al. |
| 2010/0167988 A1 | 7/2010 | Gant et al. |
| 2011/0003757 A1 | 1/2011 | Kurosaki et al. |
| 2011/0098240 A1 | 4/2011 | Dugi et al. |
| 2011/0201795 A1 | 8/2011 | Deshpande et al. |
| 2012/0041069 A1 | 2/2012 | Sesha |
| 2013/0096076 A1 | 4/2013 | Dugi et al. |
| 2013/0237487 A1 | 9/2013 | Henschke et al. |
| 2014/0243517 A1 | 8/2014 | Deshpande et al. |
| 2015/0307540 A1 | 10/2015 | Dwivedi et al. |
| 2016/0000816 A1 | 1/2016 | Broedl et al. |
| 2016/0214953 A1 | 7/2016 | Jayachandra et al. |
| 2016/0256433 A1 | 9/2016 | Staric et al. |
| 2017/0056365 A1 | 3/2017 | Sinha et al. |
| 2018/0127391 A1 | 5/2018 | Bhirud et al. |
| 2019/0038654 A1 | 2/2019 | Broedl et al. |
| 2019/0110994 A1 | 4/2019 | Shervi et al. |
| 2019/0169152 A1 | 6/2019 | Natrajan et al. |
| 2019/0175543 A1 | 6/2019 | Staric et al. |

FOREIGN PATENT DOCUMENTS

| | | | |
|---|---|---|---|
| EP | 2529742 A1 | | 12/2012 |
| IN | WO 2015/166473 | * | 11/2015 |
| WO | WO-2008002824 A1 | | 1/2008 |
| WO | WO-2008116179 A1 | | 9/2008 |
| WO | WO-2015011113 A1 | | 1/2015 |
| WO | WO-2015104658 A2 | | 7/2015 |
| WO | WO-2015128853 A1 | | 9/2015 |

(Continued)

*Primary Examiner* — Yih-Horng Shiao
(74) *Attorney, Agent, or Firm* — Blank Rome LLP

(57) ABSTRACT

The present invention relates to solid oral pharmaceutical compositions comprising amorphous dapagliflozin. The invention further relates to a process for the preparation of the said pharmaceutical compositions. The said compositions are administered orally for the treatment of diabetes mellitus. The said compositions provide the desired immediate release of dapagliflozin and were found to be stable under accelerated conditions.

12 Claims, No Drawings

(56) References Cited

FOREIGN PATENT DOCUMENTS

| WO | WO-2015198227 A1 | 12/2015 |
| WO | WO-2016098016 A1 | 6/2016 |
| WO | WO-2016161995 A1 | 10/2016 |
| WO | WO-2017118945 A1 | 7/2017 |

\* cited by examiner

PHARMACEUTICAL COMPOSITION COMPRISING DAPAGLIFLOZIN

This application is the U.S. national stage of International Patent Application No. PCT/IB2018/051221, filed Feb. 27, 2018, which claims the benefit of Indian Patent Application No. 201721009146, filed Mar. 16, 2017.

FIELD OF THE INVENTION

The present invention relates to solid oral pharmaceutical compositions comprising amorphous dapagliflozin. The invention further relates to a process for the preparation of the said pharmaceutical compositions.

BACKGROUND OF THE INVENTION

Dapagliflozin is a sodium-glucose cotransporter 2 inhibitor (SGLT2) indicated in the treatment of diabetes mellitus, in particular type 2 diabetes. It prevents reabsorption of at least 90% of the glucose in the kidney and facilitates elimination of the glucose through the urine. In the United States of America, it is available as immediate release tablets in the dose strengths of 5 mg and 10 mg under the brand name FARXIGA®. The active ingredient in FARXIGA® is a crystalline form of dapagliflozin propylene glycol hydrate.

U.S. Pat. No. 6,515,117 discloses SGLT2 inhibitor compound dapagliflozin and provides a method for treating diabetes and related disease.

U.S. Pat. No. 7,919,598 and WO2008/002824 disclose the crystalline solvates and complexes of (IS)-1, 5-anhydro-L-C-[3-((phenyl)methyl) phenyl)-D-glucitol derivatives with amino acids. In particular, the crystalline polymorphs of dapagliflozin propylene glycol hydrate is disclosed.

U.S. Pat. Nos. 8,221,786, 7,851,502, 8,716,251 and 8,361,972 disclose immediate release pharmaceutical formulation comprising dapagliflozin propylene glycol hydrate and a pharmaceutical acceptable carrier.

U.S. publication no. 2013/0237487 discloses an amorphous form of dapagliflozin.

PCT publication no. WO2015/104658 discloses amorphous form of dapagliflozin, amorphous solid dispersion of dapagliflozin together with one or more pharmaceutically acceptable carriers, process for its preparation and pharmaceutical composition thereof. The said carriers are selected from polyvinylpyrrolidones, hydroxypropylmethylcellulose, hydroxypropylcellulose, or hydroxypropylmethylcellulose acetate succinate.

U.S. publication no. 2016/0256433 discloses an amorphous solid dispersion comprising dapagliflozin and at least one polymer, a pharmaceutical composition comprising said amorphous solid dispersion and the process for its preparation. These compositions of dapagliflozin under stress and accelerated storage conditions were found to be stable for a period of 3 months.

PCT publication no. WO2015/128853 discloses pharmaceutical compositions comprising solid dispersion of dapagliflozin and one or more pharmaceutically acceptable excipients and the process for their preparation.

There is a need to provide an immediate release pharmaceutical composition comprising amorphous dapagliflozin which is stable under accelerated storage conditions of 40° C. and 75% relative humidity (RH), for a period of at least 6 months as per the recommendation of the ICH guidelines; and/or
bioequivalent to FARXIGA®

OBJECTS OF THE INVENTION

The object of present invention is to provide a stable pharmaceutical composition of amorphous dapagliflozin.

Another object of the present invention is to provide the said composition in the form of an immediate release dosage form.

It is yet another object of the present invention to provide the said composition which is bioequivalent to FARXIGA®

It is yet another object of the present invention to provide the said composition in the form of powders, granules, pellets, mini-tablets, tablets, or capsules.

It is yet another object of the present invention to provide a process for the preparation of the said compositions comprising amorphous dapagliflozin.

DETAILED DESCRIPTION OF THE INVENTION

The present invention provides pharmaceutical compositions comprising amorphous dapagliflozin and at least one surfactant.

It has surprisingly been found that the said compositions comprising amorphous dapagliflozin and at least one surfactant are stable under accelerated storage conditions of 40° C. and 75% relative humidity, for a period of at least 6 months as per the recommendation of the ICH guidelines.

It has surprisingly been found that the said compositions comprising amorphous dapagliflozin and at least one surfactant are bioequivalent to FARXIGA®.

The said compositions of the present invention provide immediate release of dapagliflozin.

The said compositions of the present invention are administered orally for the treatment of diabetes mellitus.

The compositions of the present invention further comprise at least one excipient selected from diluent, binder, disintegrating agent, antioxidant, lubricant, glidant, pigments, colouring agent, and mixtures thereof.

Dapagliflozin in accordance with the present invention is characterized by particle size distribution (PSD) as determined by the laser diffraction method (e.g. in Malvern Master Sizer). The term particle size distribution (PSD) as used herein means cumulative volume size distribution of equivalent spherical diameter.

The particle size distribution of dapagliflozin used in the preparation of the pharmaceutical composition of the present invention has d (0.9) value <250 µm, preferably in the range of 1 µm to 225 µm, more preferably in the range of 25 µm to 200 µm, and most preferably in the range of 50 µm to 175 µm.

The particle size distribution of dapagliflozin used in the preparation of the pharmaceutical composition of the present invention has d (0.5) value <100 µm, preferably in the range of 0.5 µm to 90 µm, more preferably in the range of 5 µm to 80 µm, and most preferably in the range of 10 µm to 70 µm.

The particle size distribution of dapagliflozin used in the preparation of the pharmaceutical composition of the present invention has d (0.1) value <25 µm, preferably in the range of 0.1 µm to 20 µm, more preferably in the range of 0.5 µm to 15 µm, and most preferably in the range of 1 µm to 10 µm.

In one of the embodiments the particle size distribution of the dapagliflozin used in the preparation of the pharmaceutical composition may have d (0.1) value in the range from 2 µm to 12 µm,
d (0.5) value in the range from 20 µm to 75 µm, and
d (0.9) value in the range from 75 µm to 200 µm.

Dapagliflozin is present in an amount from 0.1% to 25% by weight of the composition, preferably from 0.5% to 15%, more preferably from 1% to 7.5%, and most preferably from 2.5% to 5% by weight of the composition.

Surfactant is selected from polysorbates (for example polysorbate 20, polysorbate 40, polysorbate 60, polysorbate 65, polysorbate 80, polysorbate 85, micro-encapsulated polysorbate 80 such as SEPITRAP™ 80, micro-encapsulated polyoxyl 40 hydrogenated castor oil such as SEPITRAP™ 4000), polyoxyethylene castor oil derivatives polyoxyethylene hydrogenated castor oil (for example CREMOPHOR®), ethoxylated hydrogenated castor oil, phosphatidyl choline, phospholipids, medium chain triglycerides, docusate sodium, lecithin, glyceryl monostearate, sorbitan monostearate (SPAN® 60), sorbitan monopalmitate (SPAN® 40), sorbitan monolaurate (SPAN® 20), poloxamers (polyoxyethylene polyoxypropylene block copolymers), sodium lauryl sulfate, polyoxyethylene alkyl ethers, polyoxyethylene stearates, sorbitan fatty acid esters, sucrose esters of fatty acids, PEG-8 Caprylic-Capric glycerides (DUBCARE GPE 810), saturated polyglycolized glycerides, tocopherol PEG succinate, and mixtures thereof.

The surfactant is present in an amount from 0.1% to 25% by weight of the composition, preferably from 0.5% to 20%, more preferably from 1% to 15%, and most preferably from 2.5% to 10% by weight of the composition.

The ratio of dapagliflozin to the surfactant is usually in the range of about 1:0.1 to 1:10.

In one of the embodiments of the invention, the ratio of dapagliflozin to surfactant is in range of about 1:0.2 to 1:5, preferably in the range of about 1:0.25 to 1:3, more preferably in the range of about 1:0.3 to 1:1.5 and most preferably in the range of about 1:0.4 to 1:1.3.

Diluent is selected from anhydrous lactose, lactose monohydrate, cellulose derivatives (e.g. cellulose, microcrystalline cellulose, silicified microcrystalline cellulose) sugar, mannitol, glucose, sucrose, dextrose, fructose, compressible sugar, starches, modified starches, inorganic salts, calcium sulfate, calcium silicate, calcium phosphate, dibasic calcium phosphate, tribasic calcium phosphate, magnesium aluminometasilicate, sorbitol, xylitol, lactitol, dextran, maltodextrin, cetyl alcohol, stearyl alcohol, waxes, and mixtures thereof.

The diluent is present in an amount from 5% to 90% by weight of the composition, preferably from 10% to 85% and more preferably from 15% to 80% by weight of the composition.

Binder is selected from povidone, hydroxypropyl methylcellulose (HPMC), hydroxypropyl cellulose (HPC), hydroxyethyl cellulose (HEC), methylcellulose (MC), carboxymethylcellulose (CMC), sodium carboxymethylcellulose, calcium carboxymethylcellulose, starch paste, ethylcellulose, polymethacrylates, gelatin, polyethylene oxide, gums (example xanthan gum, guar gum, acacia, locust bean gum or alginates), polyvinyl alcohol, and mixtures thereof.

The binder is present in an amount from 0.1% to 35% by weight of the composition, preferably from 0.5% to 20%, more preferably from 1% to 10%, and most preferably from 2.5% to 7.5% by weight of the composition.

Disintegrating agent is selected from sodium starch glycolate, crospovidone, croscarmellose sodium, croscarmellose calcium, croscarmellose potassium, starch, starch 1500, modified starch, pregelatinized starch, crosslinked carboxymethyl starch, sodium hydrogen carbonate, sodium carbonate, low substituted hydroxypropyl cellulose, and mixtures thereof.

The disintegrating agent is present in an amount from 0.1% to 25% by weight of the composition, preferably from 0.5% to 15%, more preferably from 1% to 10%, and most preferably from 2.5% to 7.5% by weight of the composition.

Antioxidant is selected from butylated hydroxyanisole (BHA), butylated hydroxytoluene (BHT), sodium ascorbate, potassium sorbate, sorbic acid, sodium sulfite, tocopherol, Vitamin E derivatives, citric acid, malic acid, ascorbic acid, and mixtures thereof. The antioxidants may be present in an amount from 0.05% to 5% by weight of the composition.

Lubricant is selected from magnesium stearate, calcium stearate, stearic acid, sodium stearyl fumarate, sodium benzoate, palmitic acid, glyceryl monostearate, glyceryl behenate, and mixtures thereof. The lubricant may be present in an amount from 0.25% to 5% by weight of the composition.

Glidant is selected from suitable glidants known in the art. Examples of suitable pharmaceutically acceptable glidant are talc and colloidal silicon dioxide. The glidants may be present in an amount from 0.1% to 10% by weight of the composition.

Pigment is selected from titanium dioxide, iron oxide (e.g. iron oxide yellow, iron oxide red, iron oxide brown, iron oxide black or mixtures thereof) or mixtures thereof.

Any suitable pharmaceutically acceptable natural, semi-synthetic, or synthetic colors, and flavors may be used. Preferred colors, and flavors are those listed in the handbook of excipients.

The compositions of the present invention may be provided in the form of powders, granules, pellets, mini-tablets, tablets, or capsules.

The compositions in the form of granules, pellets, mini-tablets or tablets may optionally be coated with a film coating layer comprising film coating materials, and optionally plasticizers, colorants, pigments, lubricants, diluents and surfactants.

The film coating material is selected from hydroxypropylmethyl cellulose, hydroxypropyl cellulose, ethylcellulose, polymethacrylates, polyvinyl alcohol, Opadry®, Opadry® AMB, povidone, polyvinyl acetate, gums, waxes, and mixtures thereof. The film coating material is in the range of 0.1% to 20% by weight of the composition.

Plasticizers are selected from propylene glycol, polyethylene glycol, triacetin, triethylcitrate, acetyl triethylcitrate, acetyltributylcitrate, diethyl phthalate, dibutyl phthalate, dibutylsebacate, miglyol, hydrogenated oils, or mixtures thereof.

The plasticizer in the coating layer is present in an amount from 2.5% to 30% by weight of the coating layer, preferably from 5% to 20% by weight, more preferably from 7.5% to 15% by weight, and most preferably from 9% to 11% by weight of the coating layer.

Coating layer may be deposited on the composition using a solvent selected from water, methanol, ethanol, isopropanol, acetone, dichloromethane, ethylacetate or mixtures thereof.

The composition provides immediate release of dapagliflozin when analysed in-vitro using USP II paddle apparatus, at 60 rpm, using 1000 ml of acetate buffer having pH 4.5.

In one of the embodiments, the immediate release composition releases at least about 70% of dapagliflozin within 30 minutes.

In another embodiment, the immediate release composition releases at least about 70% of dapagliflozin within 15 minutes.

In yet another embodiment, the immediate release composition releases at least about 80% of dapagliflozin within 30 minutes.

In yet another embodiment, the immediate release composition releases at least about 80% of dapagliflozin within 15 minutes.

In yet another embodiment, the immediate release composition releases at least about 85% of dapagliflozin within 30 minutes.

In yet another embodiment, the immediate release composition releases at least about 85% of dapagliflozin within 15 minutes.

In yet another embodiment, the immediate release composition releases at least about 90% of dapagliflozin within 30 minutes.

In yet another embodiment, the immediate release composition releases at least about 90% of dapagliflozin preferably within 15 minutes.

In yet another embodiment, the immediate release composition releases at least about 90% of dapagliflozin more preferably within 10 minutes.

In yet another embodiment, the immediate release composition releases at least about 90% of dapagliflozin most preferably within 5 minutes.

In one of the embodiments, the present invention provides a method for treating type II diabetes comprising administering to a mammal in need of such treatment a pharmaceutical composition comprising therapeutically effective amount of dapagliflozin.

The composition of the present invention comprising dapagliflozin, further comprises at least one additional active ingredient.

In another embodiment, the present invention provides a method for treating type II diabetes comprising administering to a mammal in need of such treatment a pharmaceutical composition comprising therapeutically effective amount of dapagliflozin in combination with additional active ingredient(s).

The additional active ingredient may be selected from an anti-diabetic agent, an anti-hyperlipidemic agent, an anti-hypertensive agent, an anti-obesity agent, or mixtures thereof.

Examples of suitable active ingredients that can be used in combination with the dapagliflozin compositions of the present invention include: biguanides (e.g. metformin, phenformin), insulin, sulfonylureas (e.g. glyburide, glimepiride, glipizide, gliclazide, chlorpropamide), thiazolidinediones (e.g. pioglitazone, rosiglitazone, troglitazone), alpha-glucosidase inhibitors (e.g. acarabose, voglibose, miglitolol), DPP4 inhibitors (e.g. sitagliptin, vildagliptin, saxagliptin, linagliptin, alogliptin), PPAR agonist (for e.g. saraglitazar, muraglitazar, peliglitazar, tesaglitazar), meglitinides (e.g. repaglinide, nateglinide), and or other SGLT2 inhibitors (e.g. canagliflozin, ertugliflozin).

In one aspect, dapagliflozin in the compositions of the present invention is not in the form of a solid dispersion.

In another aspect, dapagliflozin in the compositions of the present invention is not in the form of a co-crystals.

The invention further relates to a process for the preparation of the said pharmaceutical compositions.

The pharmaceutical composition of the present invention may be prepared by various methods such as wet granulation, dry granulation, or direct compression.

In one aspect, the composition of the present invention is not prepared using solid dispersion technique.

In another aspect, the composition of the present invention is not prepared using co-crystals technique.

In one of the embodiments, the process for preparing the said compositions comprise steps of:
a. sifting amorphous dapagliflozin, at least one surfactant, and one or more pharmaceutically acceptable excipients selected from diluents, binders, disintegrating agents, antioxidants, lubricants, and glidants;
b. mixing the sifted material of step "a" to obtain a drug mixture;
c. filling the drug mixture of step "b" into capsules or compressing the drug mixture of step "b" into tablets;
d. optionally, film coating the tablets of step "c" to obtain film coated tablets.

In another embodiment of the invention, the process for preparing the said compositions comprise steps of:
a. sifting amorphous dapagliflozin, at least one surfactant, and one or more pharmaceutically acceptable excipients selected from diluents, binders, disintegrating agents, antioxidants, lubricants, and glidants;
b. mixing the sifted material of step "a" to obtain a drug mixture;
c. dry granulating the drug mixture of step "b" by slugging, roll compacting or any other suitable means, and further processing to give granules;
d. optionally mixing the granules of step "c" with one or more pharmaceutically acceptable excipients selected from diluents, binders, disintegrating agents, antioxidants, lubricants, and glidants;
e. filling the mixture of step "d" into capsules or compressing the mixture of step "d" into tablets;
f. optionally, film coating the tablets of step "e" to obtain film coated tablets.

In another embodiment of the invention, the process for preparing the said compositions comprise steps of:
a. sifting and mixing one or more pharmaceutically acceptable excipients selected from surfactants, diluents, binders, disintegrating agents, and antioxidants;
b. dispersing and/or dissolving amorphous dapagliflozin in a solvent selected from water, methanol, ethanol, isopropanol, acetone, dichloromethane, ethyl acetate or mixtures thereof;
c. optionally adding surfactant to the dispersion or solution of step "b";
d. granulating the mixture of step "a", with the dispersion or solution of step "c", to obtain a wet mass;
e. drying the wet mass of step "d" in a suitable dryer to obtain dried granules;
f. milling the dried granules of step "e" using a suitable mill;
g. mixing the dried granules of step "f" with one or more pharmaceutically acceptable excipients selected from diluents, binders, disintegrating agents, antioxidants, lubricants, and glidants;
h. filling the mixture of step "g" into capsules or compressing the mixture of step "g" into tablets;
i. optionally film coating the tablets of step "h" to obtain film coated tablets.

The invention is now illustrated with non-limiting examples.

Example I

TABLE 1

Composition of dapagliflozin tablets

| No. | Ingredients | % w/w |
|---|---|---|
| 1 | Amorphous Dapagliflozin [d(0.1) = 7.27 µm; d(0.5) = 58.7 µm; d(0.9) = 168 µm] | 3.92 |

TABLE 1-continued

Composition of dapagliflozin tablets

| No. | Ingredients | % w/w |
|---|---|---|
| 2 | Microcrystalline cellulose PH-101 | 54.91 |
| 3 | SEPITRAP ™ 80 | 4.90 |
| 4 | Anhydrous lactose | 19.61 |
| 5 | Low-substituted hydroxypropyl cellulose LH11 | 5.88 |
| 6 | Microcrystalline cellulose PH-112 | 6.47 |
| 7 | Colloidal silicon dioxide | 1.37 |
| 8 | Magnesium stearate | 0.98 |
| 9 | Opadry II yellow | 1.96 |

The composition of example I can be prepared by any of the manufacturing techniques as disclosed below:

Manufacturing Process (Ia):
1. Amorphous dapagliflozin, microcrystalline cellulose PH 101, SEPITRAP™ 80, anhydrous lactose, low-substituted hydroxypropyl cellulose LH11 (3.92% w/w), were sifted through 40 mesh ASTM.
2. The resulting sifted ingredients of step 1) were blended for about 15 minutes to obtain a drug mixture.
3. Microcrystalline cellulose PH-112, low-substituted hydroxypropyl cellulose LH11 (1.96% w/w), colloidal silicon dioxide and magnesium stearate were sifted through 40 mesh ASTM and mixed with the drug mixture of step 2) for about 10 minutes.
4. The resulting mixture of step 3) was compressed into tablets.
5. The resulting tablets were film coated with Opadry II yellow.

Manufacturing Process (Ib):
1. Microcrystalline cellulose PH101, anhydrous lactose, SEPITRAP™ 80, low-substituted hydroxypropyl cellulose LH11 (3.92% w/w) were sifted through 40 mesh ASTM and mixed in rapid mixer granulator (RMG) for about 10 minutes.
2. Amorphous dapagliflozin was dissolved in acetone and was added to the above mixture of step 1) to obtain a wet mass.
3. Wet mass was dried to obtain dried granules and were sifted through 30 mesh ASTM.
4. Microcrystalline cellulose PH112, low-substituted hydroxypropyl cellulose LH11 (1.96% w/w) and colloidal silicon dioxide were sifted through 30 mesh ASTM and blended with dried granules of step 3) for about 10 minutes.
5. Magnesium stearate was sifted through 40 mesh ASTM and mixed with the resulting mixture of step 4) for about 5 minutes.
6. The resulting mixture of step 5) was compressed into tablets.
7. The resulting tablets were film coated with Opadry II yellow.

Manufacturing Process (Ic):
1. Microcrystalline cellulose PH101, anhydrous lactose, low-substituted hydroxypropyl cellulose LH11 (3.92% w/w) were sifted through 40 mesh ASTM and mixed in RMG for about 10 minutes.
2. Amorphous dapagliflozin was dissolved in a mixture of isopropanol and dichloromethane (1:1) and was added to the above mixture of step 1) to obtain a wet mass.
3. Wet mass was dried to obtain dried granules and were sifted through 30 mesh ASTM.
4. Microcrystalline cellulose PH-112, low-substituted hydroxypropyl cellulose LH11 (1.96% w/w) and colloidal silicon dioxide were sifted through 30 mesh ASTM and blended with dried granules of step 3) for about 10 minutes.
5. Magnesium stearate was sifted through 40 mesh ASTM and mixed with the resulting mixture of step 4) for about 5 minutes.
6. The resulting mixture of step 5) was compressed into tablets.
7. The resulting tablets were film coated with Opadry II yellow.

Example II

TABLE 2

Composition of dapagliflozin tablets

| No. | Ingredients | % w/w |
|---|---|---|
| 1 | Amorphous Dapagliflozin<br>[d(0.1) = 3.6 µm; d(0.5) = 13 µm; d(0.9) = 27 µm] | 3.92 |
| 2 | SEPITRAP ™ 80 | 4.90 |
| 3 | Anhydrous lactose | 19.61 |
| 4 | Crospovidone | 3.92 |
| 5 | Microcrystalline cellulose PH-112 | 63.34 |
| 6 | Colloidal silicon dioxide | 1.37 |
| 7 | Magnesium stearate | 0.98 |
| 8 | Opadry II yellow | 1.96 |

Manufacturing Process (II):
1. Amorphous dapagliflozin, SEPITRAP™ 80, anhydrous lactose, crospovidone, microcrystalline cellulose PH-112, and colloidal silicon dioxide were sifted through 40 mesh ASTM.
2. The sifted ingredients of step 1) were mixed in a blender for about 15 minutes.
3. Magnesium stearate was sifted through 40 mesh ASTM and mixed with the resulting mixture of step 2) for about 5 minutes.
4. The resulting mixture of step 3) was compressed into tablets.
5. The resulting tablets were film coated with Opadry II yellow.

Example III

TABLE 3

Composition of dapagliflozin tablets

| No. | Ingredients | % w/w |
|---|---|---|
| 1 | Amorphous Dapagliflozin<br>[d(0.1) = 5.36 µm; d(0.5) = 48.8 µm; d(0.9) = 135.04 µm] | 3.92 |
| 2 | Anhydrous lactose | 19.61 |
| 3 | Dubcare GPE810 | 3.92 |
| 4 | Povidone K 30 | 3.92 |
| 5 | Microcrystalline cellulose PH-112 | 58.44 |
| 6 | Low-Substituted Hydroxypropyl Cellulose LH11 | 5.88 |
| 7 | Colloidal silicon dioxide | 1.37 |
| 8 | Magnesium stearate | 0.98 |
| 9 | Opadry II yellow | 1.96 |

Manufacturing Process (III):
1. Microcrystalline cellulose PH-112 (about 46.75% w/w), anhydrous lactose, povidone K 30 and low-substituted hydroxypropyl cellulose LH11 (about 3.92% w/w) were sifted through 40 mesh ASTM and mixed in RMG for about 10 minutes.

2. Amorphous dapagliflozin was dissolved in acetone followed by addition of Dubcare GPE 810.
3. The resulting mixture of step 2) was added to the powder mixture of step 1) in RMG to obtain a wet mass.
4. Wet mass was dried to obtain dried granules and were sifted through 30 mesh ASTM.
5. Microcrystalline cellulose PH-112 (about 11.69% w/w), low-substituted hydroxypropyl cellulose LH11 (about 1.96% w/w) and colloidal silicon dioxide were sifted through 30 mesh ASTM and blended with dried granules of step 4) for about 10 minutes.
6. Magnesium stearate was sifted through 40 mesh ASTM and mixed with the resulting mixture of step 5) for about 5 minutes.
7. The resulting mixture of step 6) was compressed into tablets.
8. The resulting tablets were film coated with Opadry II yellow.

Dissolution Profile:

The tablets prepared as per examples I to III were analysed in-vitro using USP II paddle apparatus, at 60 rpm, using 1000 ml of acetate buffer pH 4.5. The results of the dissolution testing are provided in table 4.

TABLE 4

Dissolution profile of tablets of examples I to III

| Time (mins.) | % Cumulative Dissolution Profile | | | | |
|---|---|---|---|---|---|
| | Example Ia | Example Ib | Example Ic | Example II | Example III |
| 5 | 54 | 68 | 93 | 33 | 66 |
| 10 | 78 | 95 | 100 | 48 | 92 |
| 15 | 85 | 96 | 100 | 57 | 98 |
| 20 | 89 | 96 | 100 | 62 | 97 |
| 30 | 90 | 96 | 101 | 72 | 97 |

It is evident from table 4 that the dapagliflozin compositions of the present invention provided the desired immediate release dissolution in 5 minutes to 30 minutes.

Stability Studies:

Tablet composition in accordance with example I, containing 10 mg of dapagliflozin, were packed in
i) HDPE container with 2 g silica gel and
ii) Alu-Alu blister.

These packs were subjected to accelerated storage conditions of 40° C./75% RH for a period of six months. The tablets were analysed for in-vitro dissolution, related substances and assay. The results of the accelerated stability testing at the end of six months are disclosed in table 5.

TABLE 5

Stability Study Data

| Pack | Condition | In-vitro dissolution (15 mins) | Related Substances | | | Assay |
|---|---|---|---|---|---|---|
| | | | Dapagliflozin Hydroxy Impurity | Individual Unspecified Impurity | Total Impurities | |
| Limits | Initial | NLT 80% 98% | NMT 0.5% Not detected | NMT 0.2% BQL | NMT 1.0% Nil | 90.0-110.0% 100.30% |
| HDPE Bottle | 6M 40° C./75% RH | 93% | 0.29% | 0.06% | 0.35% | 98.10% |
| Alu-Alu Blister | 6M 40° C./75% RH | 95% | 0.36% | 0.08% | 0.50% | 97.50% |

BQL: Below quantification limit
NMT: Not more than
NLT: Not less than

The stability data in table 5 reveals that there is no significant change in the in-vitro dissolution, related substances and assay value, of the dapagliflozin tablets, in both the packs, on storage. The said tablets were found to be stable for a period of at least 6 months at accelerated storage conditions (40° C./75% RH) as per the recommendation of the ICH guidelines.

Bioequivalence Study:

A randomized, open label, balanced, two treatment, two period, two sequence, single dose, crossover bioequivalence study of dapagliflozin tablets 10 mg of example I was carried out in normal healthy human subjects using Farxiga® (Dapagliflozin) tablets 10 mg of AstraZeneca Pharmaceuticals LP as the reference product.

The bioequivalence studies were carried out under fasting (n=48) and fed conditions (n=48). The % ratio of the geometric mean and the 90% CI for log transformed data are presented in table 6.

TABLE 6

Bioequivalence Data

| Parameters | Fasting Condition | | | Fed Condition | | |
|---|---|---|---|---|---|---|
| | % Ratio Test/Reference | 90% CI for log transformed data | | % Ratio Test/Reference | 90% CI for log transformed data | |
| | | Lower | Upper | | Lower | Upper |
| $C_{max}$ | 98.6772 | 91.1410 | 106.8366 | 95.8633 | 88.6893 | 103.6176 |
| $AUC_{0-72}$ | 99.7096 | 96.2435 | 103.3005 | 99.7835 | 96.7729 | 102.8878 |
| $AUC_{0-\infty}$ | 98.1155 | 94.5895 | 101.7729 | 99.4335 | 96.4915 | 102.4652 |

Based on the results of the bioequivalence studies, the dapagliflozin tablets were found to be bioequivalent to commercially available FARXIGA® tablets.

Thus, the compositions of the present invention provides the desired immediate release of dapagliflozin and was found to be bioequivalent to FARXIGA® tablets. The composition was found to be stable under accelerated conditions (40° C./75% RH) for a period of at least 6 months.

We claim:

1. A pharmaceutical tablet composition comprising:
   a) amorphous dapagliflozin having a d(0.5) in the range from 20 μm to 75 μm, and
   b) one or more surfactants, wherein (i) the weight ratio of dapagliflozin to the surfactant is from about 1:0.1 to 1:10, and (ii) the tablet is an immediate release tablet.

2. The composition as claimed in claim 1, wherein the one or more surfactant is selected from the group consisting of micro-encapsulated polysorbate 80, polysorbate 80, polysorbate 85, polysorbate 65, polysorbate 60, polysorbate 40, polysorbate 20, polyoxyethylene castor oil derivatives polyoxyethylene hydrogenated castor oil, ethoxylated hydrogenated castor oil, phosphatidyl choline, phospholipids, medium chain triglycerides, docusate sodium, lecithin, glyceryl monostearate, sorbitan monostearate, sorbitan monopalmitate, sorbitan monolaurate, poloxamers, sodium lauryl sulfate, polyoxyethylene alkyl ethers, polyoxyethylene stearates, sorbitan fatty acid esters, sucrose esters of fatty acids, PEG-8 Caprylic-Capric glycerides, saturated polyglycolized glycerides, and tocopherol PEG succinate.

3. The composition as claimed in claim 1, wherein the one or more surfactant is from about 0.1% to about 25% by weight of the composition.

4. The composition as claimed in claim 1, wherein dapagliflozin is from about 0.1% to about 25% by weight of the composition.

5. The composition as claimed in claim 1, wherein the composition further comprises at least one excipient selected from the group consisting of diluent, binder, disintegrating agent, lubricant, and glidant.

6. The composition as claimed in claim 5, wherein the disintegrating agent is selected from the group consisting of sodium starch glycolate, crospovidone, croscarmellose sodium, croscarmellose calcium, croscarmellose potassium, sodium carbonate, starch, starch 1500, modified starch, pregelatinized starch, crosslinked carboxymethyl starch, sodium hydrogen carbonate, hydroxypropyl cellulose, and mixtures thereof.

7. The composition as claimed in claim 1, wherein the composition releases at least about 70% of dapagliflozin within 30 minutes.

8. The composition as claimed in claim 1, wherein the composition is stable at 40° C. and 75% relative humidity for a period of at least six months.

9. The composition as claimed in claim 1, wherein the composition is prepared by wet granulation, dry granulation, or direct compression.

10. The composition as claimed in claim 1, wherein the composition is bioequivalent to an immediate release tablet of a crystalline form of dapagliflozin propylene glycol hydrate.

11. An immediate release tablet comprising:
    a) amorphous dapagliflozin having a d(0.5) of 20 μm to 75 μm, and
    b) a surfactant which is micro-encapsulated polysorbate 80, wherein (i) the weight ratio of dapagliflozin to the surfactant is from about 1:0.1 to 1:10, and (ii) the tablet, after storage at 40° C. and 75% relative humidity in a HDPE container or in an Alu-Alu blister for 6 months, contains no more than 1.0% of total dapagliflozin impurities.

12. The tablet of claim 11, wherein (i) the tablet comprises 5 or 10 mg of dapagliflozin and (ii) the tablet, after storage at 40° C. and 75% relative humidity in a HDPE container or in an Alu-Alu blister for 6 months, contains more than 90% of the 5 or 10 mg dapagliflozin.

\* \* \* \* \*